US011419666B2

(12) United States Patent
Batchelor et al.

(10) Patent No.: US 11,419,666 B2
(45) Date of Patent: Aug. 23, 2022

(54) ADVANCED LEVERAGE INSTRUMENT

(71) Applicant: GYRUS ACMI, INC., Southborough, MA (US)

(72) Inventors: Kester J. Batchelor, Mound, MN (US); Theodore C. Blus, Shoreview, MN (US); Tailin Fan, Nashua, NH (US); Riyad Moe, Madison, WI (US)

(73) Assignee: Gyrus ACMI, Inc., Westborough, MA (US)

( * ) Notice: Subject to any disclaimer, the term of this patent is extended or adjusted under 35 U.S.C. 154(b) by 509 days.

(21) Appl. No.: 15/089,639

(22) Filed: Apr. 4, 2016

(65) Prior Publication Data

US 2017/0281263 A1 Oct. 5, 2017

(51) Int. Cl.
| | |
|---|---|
| *A61B 18/14* | (2006.01) |
| *A61B 17/29* | (2006.01) |
| *A61B 17/30* | (2006.01) |
| *A61B 17/28* | (2006.01) |
| *A61B 90/00* | (2016.01) |

(52) U.S. Cl.
CPC .......... *A61B 18/1445* (2013.01); *A61B 17/29* (2013.01); *A61B 17/30* (2013.01); *A61B 18/1447* (2013.01); *A61B 17/2804* (2013.01); *A61B 2017/2825* (2013.01); *A61B 2017/2926* (2013.01); *A61B 2017/2937* (2013.01); *A61B 2017/2939* (2013.01); *A61B 2018/1462* (2013.01); *A61B 2090/034* (2016.02); *A61B 2090/08021* (2016.02)

(58) Field of Classification Search
CPC . A61B 17/2812; A61B 17/2816; A61B 17/30; A61B 2017/2939; A61B 2017/2947; A61B 2017/305; A61B 18/1442; A61B 18/1445; A61B 2018/1462; A61B 18/1447; A61B 2090/034; A61B 2017/2926; A45D 26/0066; A51B 2017/2939; A51B 2017/2947; A51B 2017/305
USPC ........................................ 606/205, 206, 207
See application file for complete search history.

(56) References Cited

U.S. PATENT DOCUMENTS

| | | | |
|---|---|---|---|
| 1,823,685 A | 9/1931 | Haims | |
| 4,003,380 A | 1/1977 | Wien | |
| 4,005,714 A * | 2/1977 | Hiltebrandt | A61B 18/1442 606/51 |
| 4,506,669 A * | 3/1985 | Blake, III | A61B 17/30 294/99.2 |
| 5,089,007 A * | 2/1992 | Kirsch | A61B 17/32 294/99.2 |
| 5,445,638 A | 8/1995 | Rydell et al. | |
| 5,499,997 A | 3/1996 | Sharpe et al. | |
| (Continued) | | | |

FOREIGN PATENT DOCUMENTS

EP 2554135 A1 6/2013

*Primary Examiner* — Linda C Dvorak
*Assistant Examiner* — Ryan T Clark
(74) *Attorney, Agent, or Firm* — Schwegman Lundberg & Woessner, P.A.

(57) ABSTRACT

An instrument including a first arm and a second arm. The first arm includes a first jaw including a first distal end. The second arm includes a second jaw including a second distal end. One of the first jaw and the second jaw includes a first protrusion. When the instrument is moved into a closed configuration, the first distal end and the second distal end make contact, which occurs after the first protrusion and the opposing jaw make contact.

16 Claims, 6 Drawing Sheets

(56) References Cited

U.S. PATENT DOCUMENTS

| | | |
|---|---|---|
| 5,735,849 A | 4/1998 | Baden et al. |
| 5,752,973 A | 5/1998 | Kieturakis |
| 5,849,022 A | 12/1998 | Sakashita et al. |
| 5,897,571 A | 4/1999 | Kazama |
| 6,110,171 A | 8/2000 | Rydell |
| 6,113,596 A | 9/2000 | Hooven et al. |
| 6,146,388 A | 11/2000 | McDonald |
| 6,245,070 B1 | 6/2001 | Marquis et al. |
| 6,248,123 B1 | 6/2001 | McDonald |
| 6,506,209 B2 | 1/2003 | Ouchi |
| 6,524,309 B1 | 2/2003 | Watrelot et al. |
| 6,585,733 B2 | 7/2003 | Frazier et al. |
| 6,679,882 B1 | 1/2004 | Kornerup |
| 6,916,054 B1 | 7/2005 | Baldesbesger |
| 7,473,253 B2 | 1/2009 | Dycus et al. |
| 8,317,787 B2 * | 11/2012 | Hanna ................ A61B 18/1445 606/51 |
| 8,764,769 B1 * | 7/2014 | Rodriguez-Navarro .................... A61B 17/0218 600/114 |
| 8,858,588 B2 * | 10/2014 | Sigmon, Jr. ............ A61B 17/10 606/205 |
| 9,861,362 B2 | 1/2018 | Whitman et al. |
| 2005/0049633 A1 | 3/2005 | Watanabe |
| 2006/0052777 A1 | 3/2006 | Dumbauld |
| 2009/0054894 A1 | 2/2009 | Yachi |
| 2010/0057084 A1 * | 3/2010 | Hanna ................ A61B 18/1445 606/51 |
| 2010/0305564 A1 * | 12/2010 | Livneh ................ A61B 18/1442 606/41 |
| 2011/0251608 A1 * | 10/2011 | Timm .................. A61B 17/295 606/41 |
| 2014/0005696 A1 * | 1/2014 | Schulz ............... A61B 17/1285 606/143 |
| 2014/0188159 A1 * | 7/2014 | Steege .................. A61B 17/29 606/207 |
| 2014/0230243 A1 * | 8/2014 | Roy .................. A61B 18/1445 29/874 |

* cited by examiner

ADVANCED LEVERAGE INSTRUMENT

FIELD

These teachings relate generally to an instrument for effecting an object or anatomical feature.

BACKGROUND

A forceps is a plier-like instrument that includes a pair of jaws. The forceps can be used to effect an anatomical feature. For example, the forceps can be used to grip, capture, grasp, manipulate, pull, constrict, cut, and/or dissect an anatomical feature, such as a vessel or tissue. Some forceps also include electrosurgical capabilities so that an anatomical feature can be electrically effected (e.g., cut and/or coagulated) with one or more therapy currents.

When the forceps is moved into a closed configuration, gripping forces at a proximal portion of the jaws tend to be higher than the gripping forces at a distal portion of the jaws. Accordingly, in some instances, an anatomical feature located at the proximal portion of the jaws may be damaged from the higher gripping forces. Moreover, higher gripping forces at the proximal portion of the jaws may undesirably push the anatomical feature along a length of the jaws and then "squirt" the anatomical feature from distal end thereof.

Opportunities exist for improving such instruments. For example, it may be desirable to have an instrument for effecting an anatomical feature without damaging the anatomical feature. It may be desirable to have an instrument for effecting an anatomical feature without the anatomical feature moving or "squiring off" the distal end of the jaws. Some examples of known instruments are disclosed in U.S. Pat. Nos. 6,146,388, 6,524,309, and 6,585,735, and in U.S. Patent Application Publication Number 2005/0049633, the disclosures of which are hereby incorporated by reference in their entirety.

SUMMARY

The teachings herein provide an instrument. The instrument includes opposing arms; and at least one of the arms is moveable. Each of the opposing arms may include a jaw. At least one of the arms or jaws includes a protrusion. The arms or jaws are moveable into a closed configuration where the distal ends of the jaws make contact, which occurs after the protrusion and the opposing arm or jaw makes contact. In some configurations, the jaws are moveable into a closed configuration, and after a protrusion and the opposing arm or jaw make contact, both the first jaw and the second jaw pivot about the protrusion until the distal ends make contact. In other configurations, as the jaws are moved into a closed configuration, one of the jaws pivots about the protrusion without the other jaw pivoting until the distal ends make contact.

The teachings herein provide a medical instrument comprising a first arm and a second arm. The first arm comprises a first jaw comprising a first distal end. The second arm comprises a second jaw comprising a second distal end. One of the first jaw and the second jaw comprises a first protrusion. When the medical instrument is moved into a closed configuration, the first distal end and the second distal end make contact, which occurs after the first protrusion and the opposing jaw make contact.

The teachings herein provide a medical instrument comprising a first arm and a second arm. The first arm comprises a first jaw comprising a first distal end. The second arm comprises a second jaw comprising a second distal end. One of the first jaw and the second jaw comprises a first protrusion. The first jaw is connected to the first arm with a first pivot. The first pivot is distally located relative to the first protrusion. When the medial instrument is moved into a closed configuration, the first distal end and the second distal end make contact, which occurs after the first protrusion and the opposing jaw make contact.

The teachings herein provide a medical instrument comprising a first arm and a second arm. The first arm comprises a first jaw comprising a first distal end, and a first pivot connecting the first jaw and the first arm. The second arm comprises a second jaw comprising a second distal end. One of the first jaw and the second jaw comprises a first protrusion. The first pivot is distally located relative to the first protrusion and proximally located relative to the first distal end. When the medical instrument is moved into a closed configuration, the first jaw and second jaw make contact. When the medical instrument is moved into an open configuration the first jaw and second jaw are free of contact.

DETAILED DESCRIPTION

These teachings provide an instrument. The instrument may be a medical instrument. The instrument may be a forceps. The forceps can be virtually any forceps known in the field. The instrument may be a tweezers. The instrument may be any instrument or device for effecting an object or anatomical feature. Effecting may mean, for example, holding, manipulating, engaging, moving, grasping, gripping, constricting, pushing, pulling, cutting, tearing, coagulating, sealing, cauterizing, dissecting, fulgurating, or a combination thereof an object or anatomical feature. The anatomical feature may be any anatomical feature, such as a vessel, tissue, vein, artery, the like, or a combination thereof. The instrument can be used in virtually any procedure, whether medically related or not. In medical procedures, the instrument can be used in open procedures, laparoscopic procedures, or both. The instrument may be any instrument or device having arms and/or jaws. The instrument can be a medical forceps. The instrument can be used with power. Thus, the instrument can be an electrosurgical instrument or electrosurgical forceps.

The instrument can be used with or without power. When used with power, one or more electrical currents, therapies, and/or signals may be provided to the instrument. The power, one or more electrical currents, therapies, and/or signals may be provided via a power source. The power source may be any suitable power source. The power source may be a generator. The power source may be of the type described in U.S. Pat. No. 7,282,048B2, the teachings of which are hereby incorporated by reference herein for all purposes. The one or more electrical currents, therapies, and/or signals may be provided to, through, and/or between the jaw assembly, the one or more jaws, the one or more arms, one or more electrodes, a remote pad or electrode, or a combination thereof.

The one or more electrical currents, therapies, and/or signals provided by the power source may be monopolar energy, bipolar energy, blended energy, or a combination thereof. The one or more electrical currents, therapies, and/or signals may include a cut waveform, a coagulation waveform, and/or a blended waveform. During use, an electrical circuit may be completed by passing monopolar energy from the power source to the one or more jaws, arms, and/or electrodes, to the object or anatomical feature of interest, and to a remote pad or electrode. During use, an electrical circuit may be completed by passing bipolar energy from the power source to an active electrode or active feature of the one or more arms, jaws, and/or electrodes, through the object or anatomical feature of interest, and to a return electrode or portion of jaws, arms, or a combination thereof. The cut waveform may be delivered continuously from the power source to the instrument, and can be described as a higher current/lower voltage waveform compared to the coagulation waveform. The coagulation waveform may be modulated or interrupted from the power source to the instrument, and can be described as a lower current/higher voltage waveform compared to the cut waveform. The blended waveform may be a combination of a cut waveform and a coagulation waveform. The blended waveform may advantageously allow a user to coagulate the object or anatomical feature while also cutting the object or anatomical feature. The blended waveform may be of the type described in the above-mentioned U.S. Pat. No. 7,282,048B2.

The instrument may include a hand piece. The hand piece may function to house, support, and/or contain the introducer, the arms, the jaws, or a combination thereof. The hand piece may function to house, support, and/or contain the parts, components and/or mechanism required for operating, actuating, moving, reciprocating, opening, closing, retracting, extending, rotating, and/or manipulating the introducer, the arms, the jaws, or a combination thereof. The hand piece may include sufficient controls for operating, actuating, moving, reciprocating, opening, closing, retracting, extending, rotating, and/or manipulating the arms, the jaws, the introducer, or a combination thereof. The one or more user controls may include one or more triggers, wheels, levers, buttons, knobs, the like, or a combination thereof. The hand piece may be held and/or manipulated by an operator or user with one hand or with both hands.

The instrument, the one or more arms, and/or the one or more jaws may be moveable between an open configuration and a closed or gripping configuration.

In the open configuration, instrument, the arms, and/or the jaws may be in a spaced apart relationship relative to one another. In the open configuration, a gap defined between the opposing proximal ends of the arms or jaws may be larger, smaller, or the same size as a gap defined between the opposing distal ends of the arms or jaws. In the open configuration, one or more of the protrusions may be free from contacting an opposing jaw, arm, or protrusion. In the open configuration, a gap may be defined between a protrusion and an opposing protrusion, arm, and/or jaw. In the open configuration, the arms and/or jaws may be further spaced apart relative to one another than in the closed or gripping configuration.

In the open configuration, the instrument, the arms, and/or the jaws may cooperate to effect an object or anatomic feature. In the open configuration, the instrument, the arms, and/or the jaws may exert a gripping force on the object or anatomical feature that is less than a gripping force exerted on the object or anatomical feature when the instrument, the arms, and/or jaws are in the closed configuration. In the open configuration, a suitable electrical current, therapy, and/or signal may be supplied to one or more of the arms and jaws, and may be applied to the object or anatomical feature. With a user, the hand piece, the introducer, or a mechanism in the hand piece as a reference point, when moving the instrument, the arms, and/or the jaws into the open configuration, the first arm and/or first jaw may move or pivot away from the second arm and/or second jaw; the second arm and/or second jaw may move or pivot away from the first arm and/or first jaw; both arms or jaws may move or pivot away from one another; or a combination thereof.

In the closed configuration, instrument, the arms, and/or the jaws may be in contact with one another. In the closed configuration, a distal end of the instrument, the arms, and/or the jaws may be in contact, while a proximal portion of the instrument, arms, and/or jaws are in a spaced apart relationship relative to one another. In the closed configuration, a gap defined between the opposing proximal ends of the arms or jaws may be larger, smaller, or the same size as a gap defined between the opposing distal ends of the arms or jaws. In the closed configuration, one or more of the protrusions may be in contact with an opposing jaw, arm, or protrusion. In the closed configuration, a protrusion and an opposing protrusion, arm, and/or jaw may be in contact. In the closed configuration, the arms and/or jaws may be spaced apart less relative to one another than in the open configuration.

In the closed configuration, the instrument, the arms, and/or the jaws may cooperate to effect an object or anatomic feature. In the closed configuration, the instrument, the arms, and/or the jaws may exert a gripping force on the object or anatomical feature that is greater than a gripping force exerted on the object or anatomical feature when the instrument, the arms, and/or jaws are in the open configuration. In the closed configuration, a suitable electrical current, therapy, and/or signal may be supplied to one or more of the arms and jaws, and may be passed to the object or anatomical feature. With a user, the hand piece, the introducer, or a mechanism in the hand piece as a reference point, when moving the instrument, the arms, and/or the jaws into the closed configuration, the first arm and/or first jaw may move or pivot towards the second arm and/or second jaw; the second arm and/or second jaw may move or pivot towards the second arm and/or second jaw; both arms or jaws may move or pivot towards one another; or a combination thereof.

The instrument, the arms, the jaws, or a combination thereof may be moved relative to a frame of reference. The frame of reference may be the hand piece, the one or more arms, an opposing arm, the one or more jaws, an opposing jaw, the one or ore protrusions, an opposing protrusion, a user, a patient, the anatomy, or a combination thereof. For example, one of the arms or jaws may be moved relative to the opposing arm or jaw; relative to the hand piece; relative to a user, the anatomy; or a combination thereof. For example, both of the jaws or arms may be moved relative to one another, the hand piece, a user, the anatomy, or a combination thereof.

The instrument may include one or more introducers. The introducer may function to permit a portion of the instrument to be inserted into a patient or the anatomy, while a portion of the instrument remains outside of the patient or anatomy. The introducer may function to apply a force to the one or more force receiving sections, remove a force from the one or more force receiving sections, or both. Applying a force to the one or more force receiving sections may cause the arms and/or jaws to move into a closed or gripping configuration. Removing a force to the one or more force receiving sections may cause the arms and/or jaws to move into an open configuration.

The introducer may be moveable in a first direction relative to the hand piece, the arms, or both, and/or a second direction relative to the hand piece, the arms, or both. Moving the introducer in the first direction or the second direction may cause the introducer to apply a force to the force receiving section. Moving the introducer in the first direction or the second direction may cause the introducer to remove a force from the one or more force receiving sections.

The introducer may be fixedly connected to the hand piece (e.g., not moveable), and the arms may be movable relative to the introducer and/or the hand piece. Moving the arms in the first direction or the second direction may cause the introducer to apply a force to the one or more force receiving sections. Moving the arms in the first direction or the second direction may cause the introducer to remove a force from the one or more force receiving sections.

The introducer may be an elongated, tubular member that extends along a longitudinal axis between opposing proximal and distal ends. The proximal end of the introducer may be connected to the hand piece. The distal end may be inserted into a patient or the anatomy. The one or more arms and/or jaws may extend from an inner portion of the tubular member. The introducer may be substantially straight; may include one or more angles, bends or arcs; or a combination thereof. The introducer may be substantially rigid; substantially flexible; substantially resilient; or a combination thereof.

The instrument may include one or more arms. The one or more arms may be configured to effect an object or anatomical feature. The one or more arms may function to effect an object or anatomical feature when the instrument is in an open configuration, a closed configuration, or in a position therebetween. For example, the one or more arms may be used to capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof. The one or more arms may be moved, pivoted, or flexed between an open configuration and a closed or gripping configuration, as was described above.

The one or more arms may be made of any material suitable for use in medical procedures. For example, the one or more arms may be made of steel, stainless steel, carbon steel, or a combination thereof. The one or more arms may be electrically conductive so that a therapy current can be passed to and from the arms, or the one or more arms may be electrically insulated so that a therapy current is prevented from being passed. The one or more arms are made from a material that can withstand repeated sterilization in high-temperature autoclaves. However, the arms may also be made of material suitable to be used once and then discarded, such as plastic, for example. The one or more arms may be substantially straight; may include one or more angles, bends or arcs; or a combination thereof. The one or more arms may be substantially rigid; substantially flexible; substantially resilient; or a combination thereof. The arms may be connected together at the proximal ends thereof, and may be biased or spaced apart in a steady state condition.

The first arm and the second arm may be secured together with a joint. The first arm and the second arm can be secured together so that the arms, the instrument, or both function as a lever. The lever may be a class 3 lever or a type 3 lever. A class 3 or type 3 lever may be a structure where the effort (i.e., pressure applied to the force receiving sections(s) is located between the joint or fulcrum (i.e., a cantilever pivot, a pivot joint) and the load (i.e., gripping force between the jaws). In other words, the first arm and the second arm may be secured together at a location that is proximally located to the one or more force receiving sections. The one or more force receiving sections may be proximally located relative to the first jaw and the second jaw. The arms can be secured together via a suitable joint. The arms can be connected together at only one end. For example, the joint can be a cantilever joint (See FIG. 4, for example). A cantilever joint may refer to a joint in which all degrees of freedom between the arms are constrained. The arms that are secured together via a cantilever joint may be flexible, bendable, and/or resilient. The joint may be a stationary pivot joint, which allows for rotation of one or both arms relative to one another. The arms can be secured together via a pivot joint and a biasing member or spring (See FIG. 7, for example). The biasing member or spring may maintain the arms in a spaced apart relationship when a force is not applied to one or more of the force receiving sections and/or when the arms are not caused to move or pivot. The arms that are secured together via a pivot joint may be rigid (i.e., unbendable). The pivot joint illustrated in FIG. 7 can be applied to the proximal end of a tweezers-type mechanism illustrated in FIGS. 2, 5a, and 5b, for example.

The one or more arms may be axially moveable relative to the hand piece, the introducer, or both. For example, moving the arms in the first direction or the second direction may cause the introducer to apply a force to the one or more force receiving sections. Moving the arms in the first direction or the second direction may cause the introducer to remove a force from the one or more force receiving sections. The one or more arms may be prevented from moving axially relative to the hand piece, the introducer, or both. In such cases, the introducer may be moveable so apply or remove the force from the force receiving sections.

The one or more arms may include one or more force receiving sections. The one or more force receiving sections may function to receive a force or pressure to move the instrument, the jaws, the arms, or a combination thereof into a closed or gripping position. Removing the force from the one or more force receiving sections may function to move the instrument, the arms, the jaws, or a combination thereof into an open position. When the force is removed from the force receiving sections, the instrument, the one or more arms, jaws, or a combination thereof may resilient move into an open configuration. In other words, the open configuration may be steady state.

The one or more force receiving sections may be one or more areas on the arms where application of a force causes the arms to move, bend, and/or flex into a closed position. The one or more force receiving sections may be one or more curved, raised, arcuate, or lowered portions on the one or more arms. The one or more force receiving sections may be any location of the arms proximal of the distal end of the arms and/or jaws. The one or more force receiving sections may be any location of the arms proximal of the one or more protrusions.

The force may be applied to the one or more force receiving sections along a line of action that is generally perpendicular to a longitudinal or moving axis of the introducer; a longitudinal or moving axis of the one or more arms, or both. The force may be applied to one or more force receiving sections by moving the introducer onto one or more of the force receiving sections so that an inner portion of the introducer contacts the force receiving sections; by moving the one or more arms into the introducer so that the force receiving sections contact an inner portion of the introducer; with finger pressure; or via any other suitable means.

In some instances, the force may be applied to only one of the force receiving sections (e.g., the first force receiving section) which causes that arm and/or jaw to flex towards the opposing arm and/or jaw. That is, in some instances, a force is not be applied to the opposing force receiving section (e.g., the second force receiving section); however, one skilled in the art understands an opposing reaction force is applied to the opposing force receiving section to restrain that other arm or jaw (e.g., the second arm or jaw) from moving away from the first arm and/or jaw.

The one or more arms may include one or more jaws. The one or more jaws may function to effect an object or anatomical feature. The one or more jaws may function to effect an object or anatomical feature when the instrument is in an open configuration, a closed configuration, or in a position therebetween. For example, the one or more jaws may be used to capture, grip, grasp, and/or manipulate an object or anatomical feature; provide a clamping force to secure an object or anatomical feature; provide retraction of an object or anatomical feature; provide a compression or gripping force across an object or anatomical feature; or a combination thereof.

The one or more jaws may comprise a surface to grip an object or anatomical feature. For instance, the one or more jaws may be at least partially smooth, flat, contoured, serrated, textured, horizontal, vertical, planar, canted, rolling, irregular, or a combination thereof. The one or more jaws may include one or more ridges, mouse teeth, gaps, openings, of a combination thereof. The one or more jaws may be electrically conductive so that a therapy current can be passed there through, or the one or more jaws may be electrically insulated so that a therapy current is prevented from being passed.

The one or more jaws may be integrally formed with the corresponding one or more arms. The one or more jaws may be connected to the one or more arms with a pivot. The pivot may function to provide for the corresponding jaw to move or pivot. The pivot may comprise a pin and slot about which the jaw can bend, flex, or move. The pivot may be a living hinge, which may be a thinned out area, a cut area, or a flexible area about which the jaw can bend, flex, or move.

The instrument may include one or more protrusions. The one or more protrusions may function to provide an area about which an arm or jaw can move, bend, flex, and/or rotate.

The one or more protrusions may be integrally formed with a corresponding arm or jaw. The one or more protrusions may be made of the same material or a different material as a corresponding arm or jaw. The one or more protrusions may be made from a flexible and/or resilient material. The one or more protrusions may be electrically insulating to prevent a short between the opposing arms or jaws. The one or more protrusions may be electrically conductive. The one or more protrusions may be a raised portion, surface, or area. The one or more protrusions may be a biasing member, such as a spring. The one or more protrusions may have a rounded top so that the arm and/or jaw can move, pivot, and/or rotate about the protrusion.

The one or more protrusions may be located on any part of the jaw or arm. Preferably, the one or more protrusions are located at a proximal end or proximal section of a corresponding arm or jaw. The protrusion may be located on one jaw or arm, or on both jaws or both arms. When located on both jaws or both arms, the protrusions may directly oppose one another so that the protrusions make contact when the instrument, arms, or jaws are moved into closed configuration.

The instrument may include one or more biasing members located between a jaw and corresponding arm. A biasing member may be used when a pivot is used to connect the jaw and arm. The pivot may be a suitable pivot, such as a pivot pin or even a living hinge. The biasing members may function to maintain, bias, or move an end of a jaw (i.e., a proximal end or a distal end) towards a corresponding arm. The biasing members may function to maintain, bias, or move an end of a jaw (i.e., a proximal end or a distal end) away from a corresponding arm. For example, the biasing members may be configured to maintain, bias, or move a jaw such that a distal end or portion of the jaw is moved or biased away from a corresponding arm. Accordingly, a proximal end or portion of the jaw is moved or biased towards a corresponding arm. For example, during use, the one or more biasing members may function to move or bias the distal ends of one or both of the jaws away from a corresponding arm when the arms or instrument is in an open configuration so that the distal ends of the jaws are further spaced apart in the open configuration thereby proving for a larger opening between the jaws.

The figures of this disclosure (FIGS. 1-10) illustrate exemplarity instruments and features described throughout this disclosure. It is understood that the instruments and features illustrated in a particular figure of this disclosure are not necessary limited to that one particular figure, instrument, feature, and/or embodiment. In other words, it is within the scope of this disclosure that some features from one or more instruments and/or components illustrated in the figures of this disclosure can be added, replaced, combined, substituted and/or modified with other instruments and/or features illustrated in other figures of this disclosure.

Figure 1A:
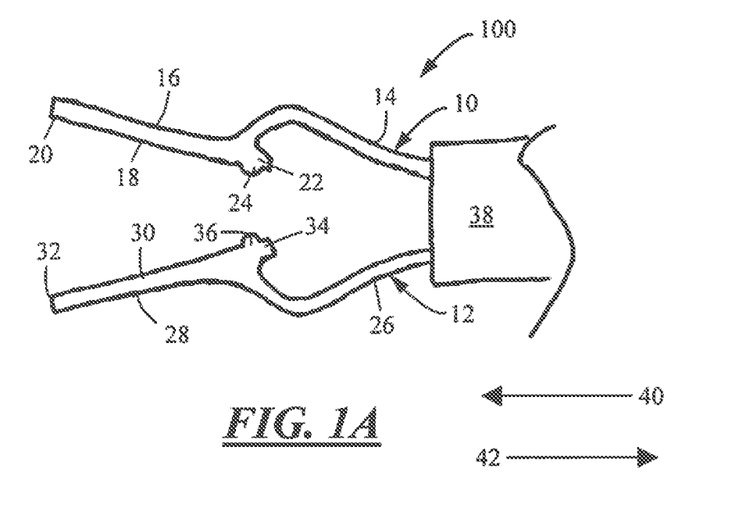
FIG. 1A is a side view of an instrument in an open configuration.
Figure 1B:
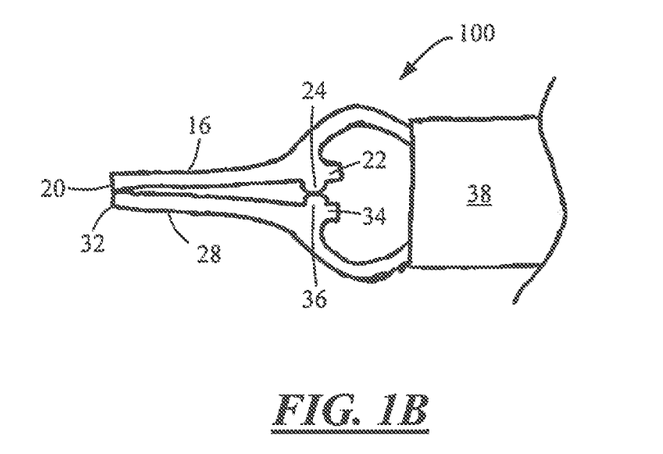
FIG. 1B is a side view of an instrument in a closed configuration.

FIGS. 1A and 1B each illustrate an instrument 100. In FIG. 1A, the instrument is shown in an open configuration. In FIG. 1B, the instrument 100 is shown in a closed or gripping configuration. The instrument 100 comprises a first arm 10 and a second arm 12. The first arm 10 comprises a first force receiving section 14 and a first jaw 16. The first jaw 16 comprises an inner surface 18 comprising a first distal end 20 and a first proximal section 22. The first proximal section 22 comprises a first protrusion 24. The second arm 12 comprises a second force receiving section 26 and a second jaw 28. The second jaw 28 comprises an inner surface 30 comprising a second distal end 32 and a second proximal section 34. The second proximal section 34 comprises a second protrusion 36. The instrument 100 comprises an introducer 38. The introducer 38 is moveable in a first direction 40 and in a second direction 42. Moving the introducer 38 in the first direction 40 causes the introducer 38 to contact and apply a force the receiving sections 14, 26, thereby causing the arms 10, 12 to move and/or flex towards one another until the protrusions 24, 36 make contact. As the introducer 38 is moved further in the first direction 40 (e.g., as the force continues to be applied to the force receiving sections 14, 26), the jaws 16, 28 pivot about the protrusions 24, 36 until the distal ends 20, 32 make contact. When the distal ends 20, 32 make contact, the rest of the inner surfaces 18, 30, including the proximal sections 22, 34, may remain spaced apart or free from making contact (FIG. 1B). When the introducer 38 is moved in the opposing second direction 42 thus removing the force from the force receiving sections 14, 26, the jaws 16, 28 pivot about the protrusions 24, 36 and the distal ends 20, 32 move away from one another. The arms 10, 12 and the jaws 16, 28 thus move and/or flex into the open configuration (FIG. 1A).

With continued reference to FIGS. 1A and 1B, rather than moving the introducer 38 in the first direction 40 and the second direction 42, the arms 10, 12 can be moved into and out of the introducer 38 by moving the arms 10, 12 in the second direction 42 and the first direction 40, respectively. That is, the arms 10, 12 can be moved in the second direction 42 into the introducer 38 so that the introducer 38 applies a force to the force receiving sections 14, 26. To remove the force from the force receiving sections 14, 26, the arms 10, 12 can be moved in the first direction 40 out of the introducer 38.

Figure 2:
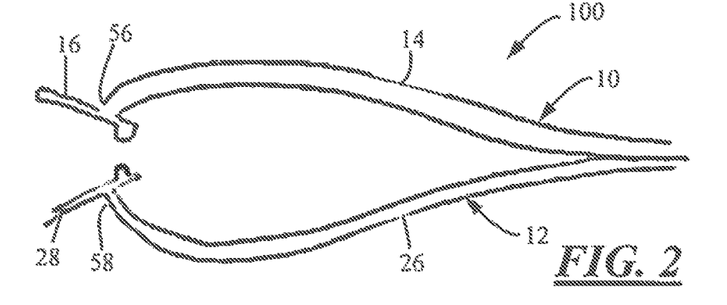
FIG. 2 is a side view of an instrument in an open configuration.

FIG. 2 illustrates an instrument 100 in an open configuration that may be substantially similar to the instrument 100 illustrated in FIG. 1A, but adds that the force applied to the force applying sections 14, 26 need not be provided via a moveable introducer 38. For example, the instrument 100 can be held or gripped by a user, and the force can be applied via finger pressure (See FIGS. 5A and 5B, for example). The first jaw 16 is connected to the first arm 10 via a first pivot 56. The second jaw 28 is connected to the second arm 12 via a second pivot 58. The instrument 100 may be a tweezers.

Figure 3:
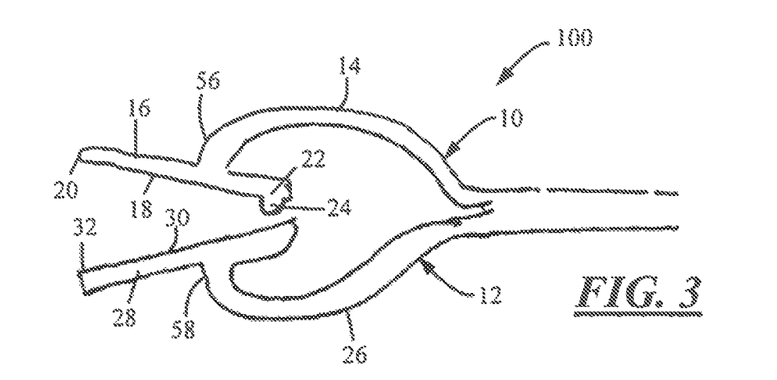
FIG. 3 is a side view of an instrument in an open configuration.

FIG. 3 illustrates an instrument 100 in an open configuration. The instrument 100 comprises a first arm 10 and a second arm 12. The first arm 10 comprises a first force receiving section 14 and a first jaw 16. The first jaw 16 is connected to the first arm 10 via a first pivot 56. The first jaw 16 comprises an inner surface 18 comprising a first distal end 20 and a first proximal section 22. The first proximal section 22 comprises a first protrusion 24. The second arm 12 comprises a second force receiving section 26 and a second jaw 28. The second jaw 28 is connected to the second arm 12 via a second pivot 58. The second jaw 28 comprises an inner surface 30 comprising a second distal end 32. The second jaw 28 is free of a protrusion. Applying a force to the force receiving sections 14, 26 causes the arms 10, 12 and the inner surfaces 18, 30 to move and/or flex towards each other until the first protrusion 24 and the opposing inner surface 30 make contact. As the force continues to be applied to the force receiving sections 14, 26, one or both of the first jaw 16 and the second jaw 28 pivots about the first protrusion 24 until the distal ends 20, 32 make contact. When the distal ends 20, 32 make contact, the rest of the inner surfaces 18, 30 may remain spaced apart from each other or free from making contact. When the force is removed from the force receiving sections 14, 26, the jaws 16, 28 pivot about the protrusion 24 and the distal ends 20, 32 move away from one another. The arms 10, 12 and the jaws 16, 28 thus move and/or flex into the open configuration.

Figure 4:
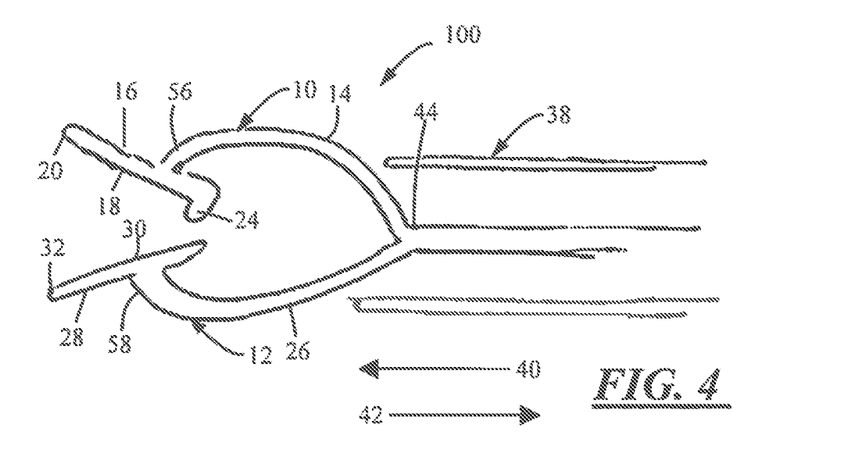
FIG. 4 is a cross-sectional view of an instrument in an open configuration.

FIG. 4 illustrates an instrument 100 in an open configuration that may be substantially similar to the instrument 100 illustrated in FIG. 3. However, the instrument illustrated in FIG. 4 adds an introducer 38. The arms 10, 12 are secured together with a joint 44. The joint 44 may be a cantilever joint. The introducer 38 is moveable in a first direction 40 and in an opposing second direction 42. Moving the introducer 38 in the first direction 40 causes the introducer 38 to contact and apply a force to each of the receiving sections 14, 26, which causes the arms 10, 12 and the inner surfaces 18, 30 to move and/or flex towards one another until the first protrusion 24 and the opposing inner surface 30 of the second jaw 28 make contact. As the introducer 38 is further moved in the first direction 40, one or both of the jaws 16, 28 pivot about the first protrusion 24 until the distal ends 20, 32 make contact. When the distal ends 20, 32 make contact, the rest of the inner surfaces 18, 30 may remain spaced apart or free from making contact. When the introducer 38 is moved in the second direction 42, and the force is removed from the force receiving sections 14, 26, the jaws 16, 28 pivot about the first protrusion 24 and the distal ends 20, 32 pivot away from one another thus moving the instrument 100 into the open configuration.

With continued reference to FIG. 4, rather than moving the introducer 38 in the first direction 40 and the second direction 42, the arms 10, 12 can be moved into and out of the introducer 38 by moving the arms 10, 12 in the second direction 42 and the first direction 40, respectively. That is, the arms 10, 12 can be moved in the second direction 42 into the introducer 38 so that the introducer 38 applies a force to the force receiving sections 14, 26. The arms 10, 12 can be moved in the first direction 40 out of the introducer 38 to remove the force from the force receiving sections 14, 26.

Figure 5A:
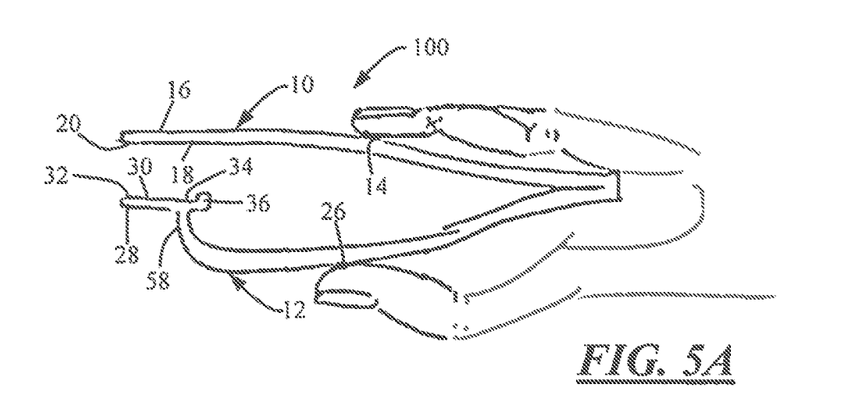
FIG. 5A is a side view of an instrument in an open configuration.
Figure 5B:
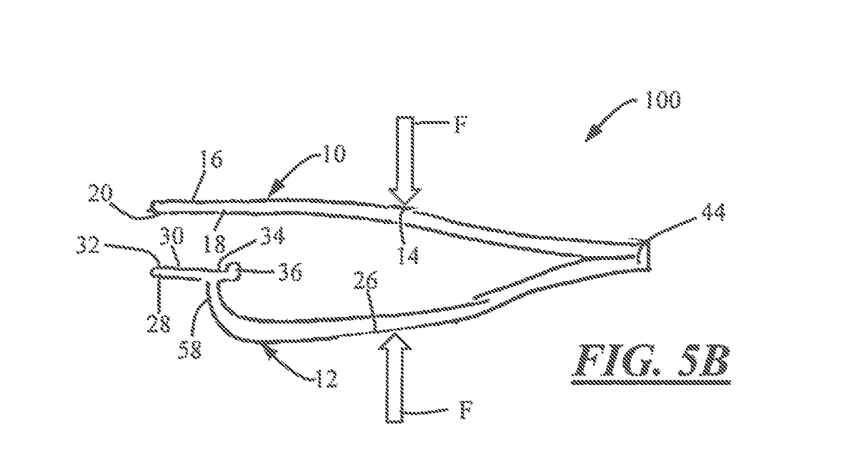
FIG. 5B is a side view of an instrument in an open configuration.

FIGS. 5A and 5B illustrate an instrument 100 in an open configuration. The instrument 100 may be a tweezers. The instrument 100 comprises a first arm 10 and a second arm 12. The first arm 10 comprises a first force receiving section 14 and a first jaw 16. The instrument 100 is free from any pivots or pins connecting the first jaw 16 and the first arm 10. The first jaw 16 comprises an inner surface 18 having a first distal end 20. The second arm 12 comprises a second force receiving section 26 and a second jaw 28. The second jaw 28 is connected to the second arm 12 via a second pivot 58. The second jaw 28 comprises an inner surface 30 having a second distal end 32, a second proximal section 34, and a second protrusion 36. The first arm 10 and the second arm 12 are joined or secured together via a joint 44, which may be a cantilever joint. The joint 44 is proximally located relative to the first and second force receiving sections 14, 26. The force receiving sections 14, 26 are proximally located relative to the first and second jaws 16, 28. Applying a force F (FIG. 5B) to the force receiving sections 14, 26 causes the arms 10, 12 and the inner surfaces 18, 30 to move or flex towards another until the second protrusion 36 and the inner surface 18 of the first jaw 16 make contact. The instrument 100 can be held or gripped by a user, and the force on the force receiving sections 14, 26 can be applied via finger pressure (e.g., via index finger and thumb; FIG. 5A). As the forces continue to be applied to the force receiving sections 14, 26, one or both of the first jaw 16 and the second jaw 28 pivots about the second protrusion 36 until the distal ends 20, 32 make contact. When the distal ends 20, 32 make contact, the rest of the inner surfaces 18, 30 may be spaced apart or free of contact.

Figure 6:
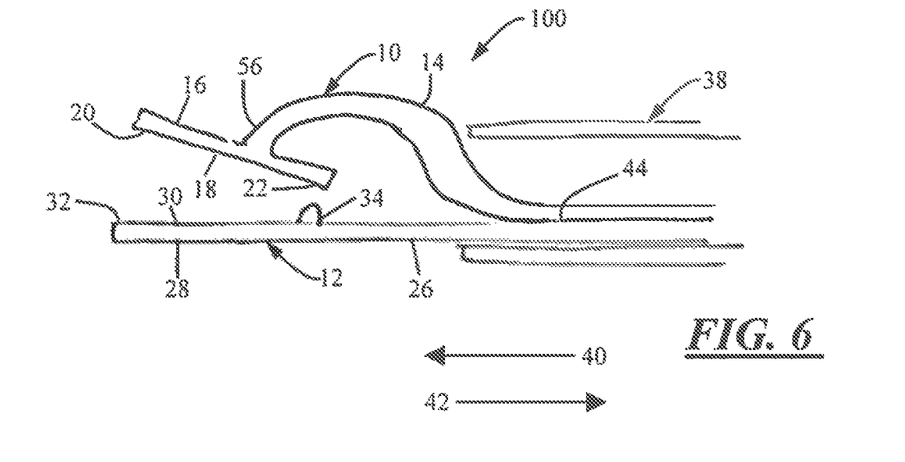
FIG. 6 is a cross-sectional view of an instrument in an open configuration.

FIG. 6 illustrates an instrument 100 in an open configuration. The instrument 100 comprises a first arm 10 and a second arm 12. The first arm 10 comprises a first force receiving section 14 and a jaw first 16. The first jaw 16 is connected to the first arm 10 via a first pivot 56. The first jaw 16 comprises an inner surface 18, a first distal end 20, and a first proximal section 22. The second arm 12 comprises a second force receiving section 26 and a second jaw 28. The instrument 100 is free from any pivots or pins connecting the second jaw 28 and the second arm 12. The second jaw 28 comprises an inner surface 30 having a second distal end 32 and a second protrusion 34. The instrument 100 comprises an introducer 38. The introducer 38 is moveable in a first direction 40 and in a second direction 42. The first arm 10 and the second arm 12 are joined or secured together via a joint 44, which may be a cantilever joint. The joint 44 is proximally located relative to the first and second force receiving sections 14, 26. The force receiving sections 14, 26 are proximally located relative to the first and second jaws 16, 28. Moving the introducer 38 in the first direction 40 causes the introducer 38 to contact and apply a force to the receiving sections of at least the first arm 14, which causes at least the first arm 10, to move and/or flex towards the second arm until the second protrusion 34 and the proximal section 22 of the first jaw 18 make contact. As the introducer 38 is further moved in the first direction 40, one or both of the first jaw 16 and the second jaw 18 pivots about the protrusion 34 until the distal ends 20, 32 make contact thus moving the instrument 100 into the closed configuration. When the distal ends 20, 32 make contact, the rest of the inner surfaces 18, 30 may be spaced apart or free of contact.

With continued reference to FIG. 6, rather than moving the introducer 38 in the first direction 40 and the second direction 42, the arms 10, 12 can be moved into and out of the introducer 38 by moving the arms 10, 12 in the second direction 42 and the first direction 40, respectively. That is, the arms 10, 12 can be moved in the second direction 42 into the introducer 38 so that the introducer 38 applies a force to the force receiving sections 14, 26. The arms 10, 12 can be moved in the first direction 40 out of the introducer 38 to remove the force from the force receiving sections 14, 26.

Figure 7:
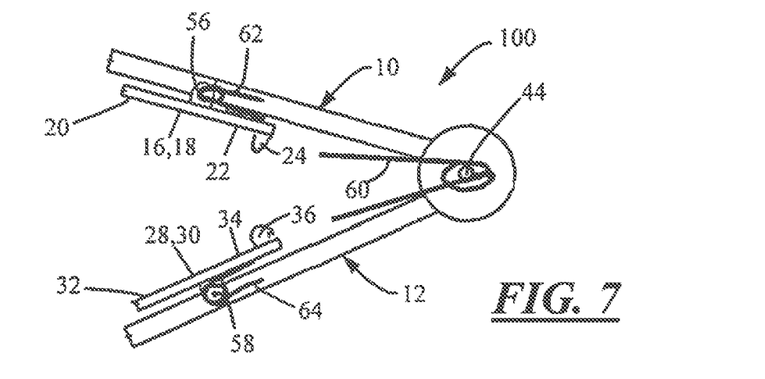
FIG. 7 is a side view of an instrument in an open configuration.

FIG. 7 illustrates an instrument 100 in an open configuration. The instrument 100 comprises a first arm 10 and a second arm 12. The arms 10, 12 are connected with a joint 44 that is may be a stationary pivot joint. A biasing member 60 located between the arms 10, 12 maintains the instrument 100 in the open configuration in a steady state configuration (e.g., when the arms 10, 12 are not being moved or biased towards each other). The first arm 10 comprises a first jaw 16 connected to the first arm 10 via a first pivot 56. A biasing member 62 is located between the first arm 10 and the first jaw 16. The biasing member 62 is configured to maintain, bias, or move, the first jaw 16 such that the proximal portion 22 is biased away from the first arm 10 and the distal portion 20 is moved or biased towards the arm 10 The first jaw 16 comprises an inner surface 18, a first distal end 20, and a first proximal section 22. The first proximal section 22 comprises a first protrusion 24. The second arm 12 comprises a second jaw 28 that is connected to the second arm 12 via a second pivot 58. A biasing member 64 is located between the arm 12 and the jaw 28. The biasing member 64 is configured to maintain, bias, or move, the second jaw 18 such that the proximal portion 34 is biased away from the first arm 12 and the distal portion 32 is moved or biased towards the arm 12. The second jaw 28 comprises an inner surface 30, a second distal end 32, and a second proximal section 34. The second proximal section 34 comprises a second protrusion 36. The instrument 100 can be moved into the closed configuration by overcoming the spring force of the biasing member 60 and causing the arms 10, 12 to pivot towards each other about the joint 44 until the protrusions 24, 36 make contact. The arms 10, 12 may be rigid so that when the arms 10, 12 pivot or rotate towards one another, the arms 10, 12 do not flex or bend. The arms 10, 12 can be moved by applying a force to the force receiving sections of the first arm and the second arm. The jaws 16, 28 can then pivot about the pivots 24, 36 while overcoming the spring force of the respective biasing members 62, 64, until the distal ends 20, 32 make contact. When the distal ends 20, 32 make contact, the rest of the inner surfaces 18, 30 may be spaced apart or free of contact.

Figure 8:
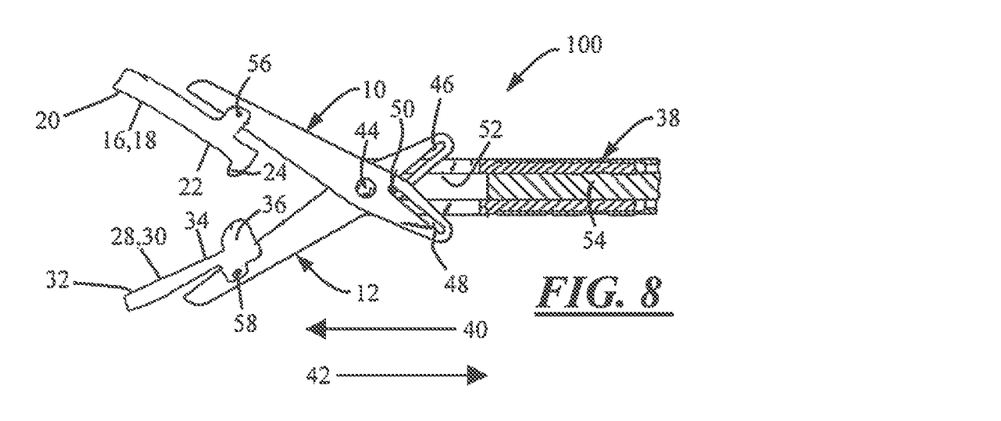
FIG. 8 is a cross-sectional view of an instrument in an open configuration.

FIG. 8 illustrates an instrument 100 in an open configuration. The instrument 100 comprises a first arm 10 and a second arm 12. The first arm 10 comprises a first jaw 16 that is connected to the first arm 10 with a first pivot 56 that may be a pivot pin. The first jaw 16 comprises an inner surface 18, a first distal end 20, and a first proximal section 22. The first proximal section 22 comprises a first protrusion 24. The second arm 12 comprises a second jaw 28 that is connected to the second arm 12 with a second pivot 58. The second jaw 28 comprises an inner surface 30, a second distal end 32, and a second proximal section 34. The second proximal section 34 comprises a second protrusion 36. The instrument comprises a joint 44 that may be a stationary pivot joint connecting the arms 10 12; a slot 46 in the second arm 12, a slot 48 in the first arm 10; and an actuator 54 connected to a pin 50. The actuator 54 is moveable within a slot 52 in the introducer 38. The actuator 54 is moveable in the first and second directions 40, 42, and the pin 50 connected to the actuator is thus moveable within the slots 46, 48. As the actuator 54 is moved in the first direction 40, the pin 50 slides within the slots 46, 48 causing the arms 10, 12 to pivot about the stationary pivot 44 towards each other until the protrusions 24, 36 make contact. As the actuator 54 continues to be moved in the first direction 40, the jaws 16, 28 pivot about the protrusions 24, 36 until the distal ends 20, 32 make contact. When the distal ends 20, 32 make contact, the rest of the inner surfaces 18, 30 may be spaced apart or free of contact. To move the instrument 100 into the open configuration, the actuator 54 can be moved in the second direction 42 thus causing the pin 50 to move in an opposing direction in the slots 46, 48 so that the arms 10, 12 move or pivot away from each other.

Figure 9:
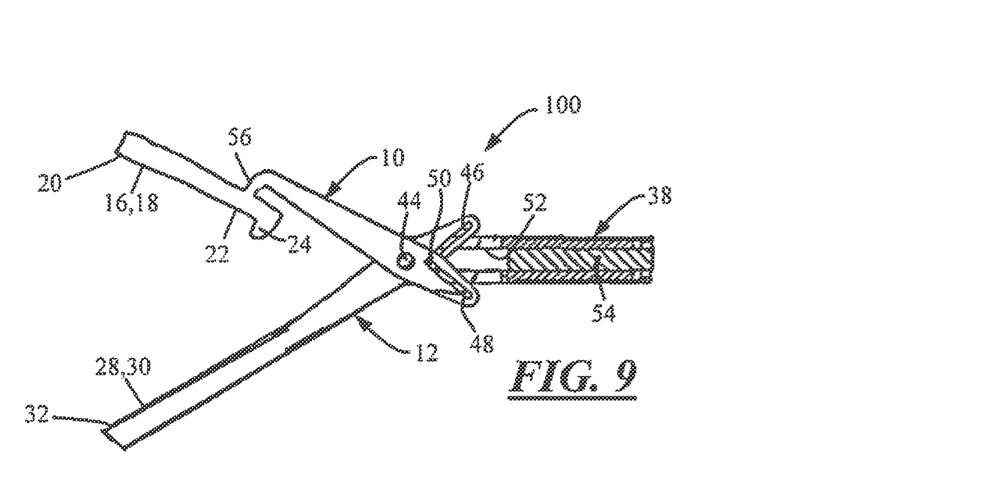
FIG. 9 is a cross-sectional view of an instrument in an open configuration.

FIG. 9 illustrates an instrument 100 in an open configuration. The instrument 100 illustrated in FIG. 9 may be substantially similar to the instrument 100 illustrated in FIG. 8. The first jaw 16 is connected to the first arm 10 via a first pivot 56 that may be a living hinge. The living hinge may be a thinner or narrowed section of material between the first arm 10 and the jaw 22 so that the jaw 22 rotates relative to the arm 10 by flexing or bending at the living hinge. The instrument 100 is free from any pivots or pins connecting the second jaw 28 and the second arm 12. Moreover, the second jaw 28 is free of a second protrusion 36. Moving the actuator 54 in the first direction 40 causes the pin 50 to slide within the slots 46, 48 so that the arms 10, 12 pivot about the joint 44 that may be a stationary pivot joint towards each other until the first protrusion 24 and the inner surface 30 of the second jaw 28 make contact. As the actuator 54 continues to be moved in the first direction 40, one or both of the first jaw 16 and the second jaw 28 pivots about the first protrusions 24 until the distal ends 20, 32 make contact. When the distal ends 20, 32 make contact, the rest of the inner surfaces 18, 30 may be spaced apart. Moving the actuator in the second direction 42 causes the pin 50 to move in an opposing direction so that the arms 10, 12 move away from each other.

Figure 10:
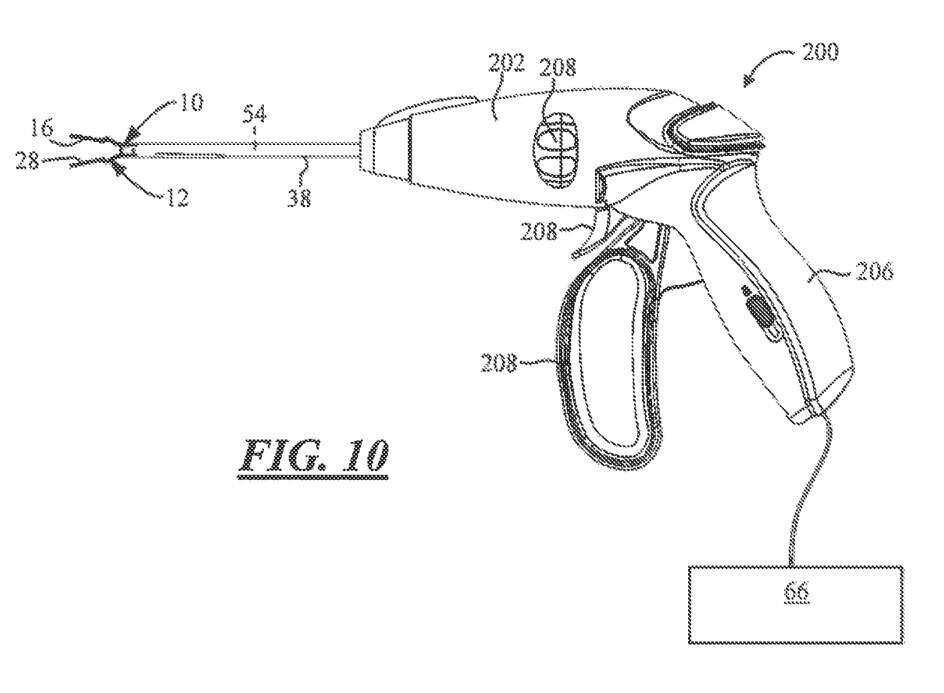
FIG. 10 is a side view of an instrument in an open configuration.

FIG. 10 illustrates an instrument 200. The instrument comprises a hand piece 206 and one or more controls 208 for moving the introducer 38. Extending from within the introducer 38 is a first arm 10 and a second arm 12, which may be any of the arms disclosed herein. Manipulating one or more of the controls 208 causes the introducer 38 to move in the first or second direction to apply or remove, respectively, a force to the force receiving sections 14, 26 to move the arms 10, 12 into the closed or open configurations. Manipulating one or more of the controls 208 causes the arms 10, 12 to move in the second or first direction, out of and in to the introducer 39, to apply or remove, respectively, a force to the force receiving sections 14, 26 to move the arms 10, 12 into the closed or open configurations. Manipulating one or more of the controls 208 causes the actuator 54 located within the introducer 38 to move in the first or second direction to move the arms 10, 12 into the closed or open configurations. One or both of the first jaw and the second jaw 16, 28 may include an electrode that is in communication with a generator 66 supplying one or more therapy currents.

The explanations and illustrations presented herein are intended to acquaint others skilled in the art with the teachings, its principles, and its practical application. Those skilled in the art may adapt and apply the teachings in its numerous forms, as may be best suited to the requirements of a particular use. Accordingly, the specific embodiments of the present teachings as set forth are not intended as being exhaustive or limiting of the teachings. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. Other combinations are also possible as will be gleaned from the following claims, which are also hereby incorporated by reference into this written description.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner. As can be seen, the teaching of amounts expressed as "parts by weight" herein also contemplates the same ranges expressed in terms of percent by weight. Thus, an expression in the Detailed Description of the Teachings of a range in terms of at "'x' parts by weight of the resulting polymeric blend composition" also contemplates a teaching of ranges of same recited amount of "x" in percent by weight of the resulting polymeric blend composition."

Unless otherwise stated, all ranges include both endpoints and all numbers between the endpoints. The use of "about" or "approximately" in connection with a range applies to both ends of the range. Thus, "about 20 to 30" is intended to cover "about 20 to about 30", inclusive of at least the specified endpoints.

The disclosures of all articles and references, including patent applications and publications, are incorporated by reference for all purposes. The term "consisting essentially of" to describe a combination shall include the elements, ingredients, components or steps identified, and such other elements ingredients, components or steps that do not materially affect the basic and novel characteristics of the combination. The use of the terms "comprising" or "including" to describe combinations of elements, ingredients, components or steps herein also contemplates embodiments that consist essentially of the elements, ingredients, components or steps.

Plural elements, ingredients, components or steps can be provided by a single integrated element, ingredient, component or step. Alternatively, a single integrated element, ingredient, component or step might be divided into separate plural elements, ingredients, components or steps. The disclosure of "a" or "one" to describe an element, ingredient, component or step is not intended to foreclose additional elements, ingredients, components or steps.

It is understood that the above description is intended to be illustrative and not restrictive. Many embodiments as well as many applications besides the examples provided will be apparent to those of skill in the art upon reading the above description. The scope of the teachings should, therefore, be determined not with reference to the above description, but should instead be determined with reference to the appended claims, along with the full scope of equivalents to which such claims are entitled. The disclosures of all articles and references, including patent applications and publications, are incorporated by reference for all purposes. The omission in the following claims of any aspect of subject matter that is disclosed herein is not a disclaimer of such subject matter, nor should it be regarded that the inventors did not consider such subject matter to be part of the disclosed inventive subject matter.

The invention claimed is:

1. A medical instrument comprising:
   a. a first arm having a distal end and comprising:
      i. a first jaw comprising a first proximal end and a first distal end, wherein the first proximal end and the first distal end are coplanar and define a first inner surface; and
   b. a second arm having a distal end comprising:
      i. a second jaw comprising a second distal end;
      wherein the first jaw comprises a first protrusion proximate the first proximal end, the first protrusion projects from the first jaw in a direction of the second jaw, wherein the first protrusion is above a plane defined by the coplanar first proximal end and first distal end;
      wherein the second jaw comprises a flat surface extending from the second distal end to a second proximal end defining a planar surface and defining a second inner surface facing the first inner surface with no protrusions rising above the flat surface of the second jaw, and
      wherein the first distal end of the first jaw extends distally past the distal end of the first arm and the second distal end of the second jaw extends distally past the distal end of the second arm;

wherein during movement of the medical instrument into a closed configuration around an anatomical feature, the first distal end of the first jaw and the second distal end of the second jaw make contact, which occurs after the first protrusion and the flat surface make contact, and wherein during movement into the closed configuration, the first jaw and the second jaw defining a pivoting movement of the first jaw relative to the second jaw from when the first protrusion and the flat surface make contact until the first distal end of the first jaw and the second distal end of the second jaw make contact, wherein when the first distal end and the second distal end make contact, the rest of the first and second inner surfaces remain spaced apart and free from making contact.

2. The medical instrument of claim 1, wherein after the first protrusion and the flat surface make contact, one of the first jaw and the second jaw pivots about the first protrusion without the other jaw pivoting until the first distal end and the second distal end make contact.

3. The medical instrument of claim 1, wherein after the first protrusion and the flat surface make contact, both the first jaw and the second jaw pivot about the first protrusion.

4. The medical instrument of claim 1, wherein the first arm comprises a first force receiving section and the second arm comprises a second force receiving section, and
wherein moving the medical instrument into the closed configuration comprises applying a force to the first force receiving section and to the second force receiving section so that the first jaw and the second jaw are moved towards one another.

5. The medical instrument of claim 4, wherein the medical instrument comprises a tubular introducer extending from a hand piece, and
wherein the force is applied to the first force receiving section and the second force receiving section by moving the introducer over the first force receiving section and the second force receiving section.

6. The medical instrument of claim 4, wherein the medical instrument is configured to be gripped by a user, and the force applied to the first force receiving section and the second force receiving section is finger pressure.

7. The medical instrument of claim 1, wherein the first jaw comprises a first tissue contacting surface having a length extending between the first proximal end and the first distal end; and
wherein the length of the first protrusion is less than the length of the first tissue contacting surface.

8. The medical instrument according to claim 1, wherein the second jaw comprises a proximal end, and the proximal end and the second distal end are coplanar.

9. The medical instrument of claim 1, wherein the first projection is non-electrically conductive.

10. The medical instrument of claim 1, wherein the first protrusion has a rounded top, and the first jaw rotates about the first protrusion during movement of the medical instrument into the closed configuration.

11. A medical instrument comprising:
a. a first arm comprising:
i. a first jaw comprising a first proximal end and a first distal end and having a first inner surface;
ii. a first pivot located at a midsection of the first jaw between a distal end and a proximal end of the first jaw and connecting the first jaw and the first arm and providing for the first jaw to move relative to the first arm; and
iii. a biasing member located at the first pivot between the first arm and the first jaw, wherein the biasing member is positioned at the midsection of the first jaw between the first proximal end and the first distal end of the first jaw such that the biasing member is configured to bias a proximal portion of the first jaw away from the first arm and bias a distal portion of the first jaw towards the first arm, and such that when the distal end of the first jaw moves towards the first arm the proximal end of the first jaw moves away from the first arm and when the distal end of the first jaw moves away from the first arm the proximal end of the first jaw moves towards the first arm;
b. a second arm comprising:
iii. a second jaw comprising a second distal end and having a second inner surface facing the first inner surface;
wherein one of the first jaw and the second jaw comprises a first protrusion that extends in a direction of the other of the first jaw and the second jaw,
wherein when the medical instrument is moved into a closed configuration around an anatomical feature, a distal end of the first jaw and a distal end of the second jaw make contact, which occurs after the first protrusion and the other of the first jaw and the second jaw make contact, and wherein during movement into the closed configuration, the first jaw and the second jaw defining a pivoting movement of the first jaw relative to the second jaw from when the first protrusion and the flat surface make contact until the first distal end of the first jaw and the second distal end of the second jaw make contact, wherein when the first distal end and the second distal end make contact, the rest of the first and second inner surfaces remain spaced apart and free from making contact.

12. The medical instrument of claim 11, wherein the second jaw is connected to the second arm with a second pivot that provides for the second jaw to move relative to the second arm, and
wherein the second arm comprises a biasing member located between the second arm and the second jaw.

13. The medical instrument of claim 11, wherein when the medical instrument is moved into the closed configuration, the distal end of the first jaw and the distal end of the second jaw make contact, which occurs after the first protrusion and a second protrusion provided on the other of the first jaw and the second jaw make contact.

14. The medical instrument of claim 11, wherein when the medical instrument is moved into the closed configuration, the distal end of the first jaw and the distal end of the second jaw make contact, which occurs after the first protrusion and a flat surface provided on the other of the first jaw and the second jaw make contact.

15. A medical instrument comprising:
a. a first arm having a distal end and comprising:
a first jaw comprising a first proximal end and a first distal end, wherein the first proximal end and the first distal end are coplanar and define a first inner surface; and
b. a second arm having a distal end and comprising:
a second jaw comprising a second proximal end and a second distal end, wherein the second proximal end and the second distal end are coplanar, wherein the second jaw comprises a flat surface extending from the second distal end to the second proximal end defining a planar surface with no protrusions rising above the flat surface of the second jaw and defining a second inner surface facing the first inner surface;

wherein the first jaw comprises a first protrusion that extends in a direction of the second jaw, wherein the first protrusion is above a plane defined by the coplanar first proximal end and first distal end of the first jaw, and wherein the first distal end of the first jaw extends distally past the distal end of the first arm and the second distal end of the second jaw extends distally past the distal end of the second arm;

wherein when the medical instrument is moved into a closed configuration around an anatomical feature, the first distal end and the second distal end make contact, which occurs after the first protrusion and the flat surface of the second jaw make contact, and wherein after the protrusion and the second jaw make contact, the first jaw pivots about the protrusion without the second jaw pivoting and wherein during movement into the closed configuration, the first jaw and the second jaw defining a pivoting movement from when the first protrusion and the flat surface make contact until the first distal end of the first jaw and the second distal end of the second jaw make contact, wherein when the first distal end and the second distal end make contact, the rest of the first and second inner surfaces remain spaced apart and free from making contact.

16. The medical instrument of claim 15, wherein the first jaw is configured to pivot after the protrusion and the opposing jaw make contact.

\* \* \* \* \*